United States Patent [19]

Yodice et al.

[11] Patent Number: 5,023,133
[45] Date of Patent: Jun. 11, 1991

[54] ACID SENSOR

[75] Inventors: Richard Yodice, Willoughby; Richard E. Gapinski, Mentor, both of Ohio

[73] Assignee: The Lubrizol Corporation, Wickliffe, Ohio

[21] Appl. No.: 474,236

[22] Filed: Feb. 1, 1990

Related U.S. Application Data

[60] Continuation of Ser. No. 231,126, Aug. 11, 1988, abandoned, which is a division of Ser. No. 941,018, Dec. 12, 1986, abandoned.

[51] Int. Cl.⁵ .............................................. B32B 27/00
[52] U.S. Cl. .................................. 428/332; 252/500; 428/339; 428/402; 528/422
[58] Field of Search ................. 428/332, 339, 402; 528/422; 252/500

[56] References Cited

U.S. PATENT DOCUMENTS

| | | | |
|---|---|---|---|
| 2,122,578 | 7/1938 | McMaster et al. | 175/123 |
| 4,030,028 | 6/1977 | Allender | 324/65 |
| 4,237,194 | 12/1980 | Upsonetal | 428/424.2 |
| 4,324,761 | 5/1982 | HArris | 422/98 |
| 4,401,544 | 8/1983 | Naarmann et al. | 204/291 |
| 4,411,741 | 10/1983 | Janata | 204/1 |
| 4,434,233 | 2/1984 | Bzdula | 436/60 |
| 4,444,892 | 4/1984 | Malmros | 436/528 |
| 4,532,188 | 7/1985 | Naarmann et al. | 428/500 |
| 4,543,402 | 9/1985 | Traynor | 526/258 |
| 4,560,534 | 12/1985 | Kung | 422/68 |
| 4,563,263 | 1/1986 | Oyama et al. | 204/418 |
| 4,579,641 | 4/1986 | Shimomura et al. | 204/403 |
| 4,582,589 | 4/1986 | Ushizawa et al. | 204/433 |
| 4,638,286 | 1/1987 | Nichols | 338/34 |
| 4,691,167 | 9/1987 | Vlekkert et al. | 324/438 |
| 4,698,657 | 10/1987 | Watanabe et al. | 357/25 |

FOREIGN PATENT DOCUMENTS

| | | |
|---|---|---|
| 1206079 | 6/1986 | Canada . |
| 61-44339 | 3/1986 | Japan . |
| 840020 | 1/1984 | South Africa . |

OTHER PUBLICATIONS

Electrically Conducting Polymers, Waltman et al, 1986, pp. 76-95.
Polyaniline, MacDairmid, 1985, pp. 173-180.
Enhanced Stability of Photoelectrodes with Electro Generated Polyaniline Films, Noufi et al, pp. 2261-2265.
Ohmec, David Allender, 8/24/84, 2 pgs.
Ohmec New Product Announcement, Warming System 3 pgs.
Ohmec Model 100 Oil Contaminant, 2 pgs.

*Primary Examiner*—Morton Foelak
*Attorney, Agent, or Firm*—Forrest L. Collins; Frederick D. Hunter; Robert A. Franks

[57] ABSTRACT

The present invention describes devices capable of sensing changes of acidity in a non-aqueous medium. The devices are particularly useful for determining the alkaline reserve in a motor vehicle lubricating oil.

13 Claims, 1 Drawing Sheet

ACID SENSOR

This is a continuation of co-pending Ser. No. 231,126, filed Aug. 11, 1988, now abandoned, which is a division of co-pending Ser. No. 941,018, filed on Dec. 12, 1986, now U.S. Pat. No. 4,791,374,

BACKGROUND OF THE INVENTION

1. Field of the Invention

This invention describes a method, and an apparatus for practicing the method wherein acidic hydrogen concentration may be determined in a substantially non-aqueous medium. The invention also describes determining the acidic hydrogen concentration in a substantially aqueous medium wherein the hydrogen ion concentration is relatively low.

2. Description of the Art

It has been known for several years that lubricating oils, particularly those lubricating oils utilized in diesel or gasoline internal combustion engines, become contaminated. A major source of the contamination is due to the presence of acids such as sulfur or nitrogen containing acids. These acids are, of course, extremely corrosive to various engine parts and are ordinarily controlled by placing substantial amounts of metal bases in the lubricating oil. The function of the metal base in the lubricating oil is to neutralize the acids which are formed in the lubricating oil. The sulfur and nitrogen containing acids are typically formed from the oxidation of sulfur in the fuel and through nitrogen oxide formation during the combustion process. Additional acids are formed in the lubricating oil through free radical mechanisms. When the alkaline reserve (metal base) is depleted, the lubricating oil is no longer able to protect the engine parts against the corrosive effects of the various acids.

It is desirable to be able to determine the acidity of the oil at any given point in time due to the damage which occurs when acid build up is observed. The damage includes corrosivity, depletion of anti-oxidants and viscosity rise. In the case of passenger automotive vehicles, the manufacturer typically recommends changing the oil at set periods of time or after a certain mileage interval has been reached. The practice is particularly dangerous in the case of stop and go driving conditions where the acids rapidly build up due to poor engine operating conditions, e.g., short trips and a cold engine. In large diesel engines, the fleet owners typically have the oil analyzed at set periods to determine, among other items, the alkaline reserve balance in the oil. These tests are done because the large diesel engines often contain 100 liters or more of lubricating oil. Thus, a fleet owner may analyze the oil at a cost of a few dollars as opposed to the much larger cost of changing the engine oil.

In either the passenger car or the diesel fleet owner situation, the risk is present that the oil acidity will change too rapidly to be detected by either a standard interval oil change or an analysis. Thus, it is highly desirable to be able to monitor the acid build up within a lubricating oil on a substantially on-going basis. That is, if the engine operator were presented with adequate sensing means to determine the point at which the oil becomes relatively acid, then the oil may be changed at the point at which it is actually required.

As a standard pH meter is unable to operate within an oil of lubricating viscosity, it is desirable for practical means to be developed to determine the acid content in a substantially non-aqueous medium. While the amount of water in an engine oil is insufficient to allow a pH meter to operate, there is nonetheless sufficient water present to present substantially all of the acid species within the oil in a state wherein severe corrosion will result. This small amount of water within the lubricating oil also is sufficient to carry the acid species uniformly throughout the oil, thus, allowing a sensing means, to determine if available acid species are becoming more prevalent in the oil.

It is known from an article entitled "Electrically Conducting Polymers:A Review of the Electropolymerization Reaction, of the Effects of Chemical Structure on Polymer Films, and of Applications Toward Technology", authored by Waltman and Bargon in the Can. J. Chem. 64, 76(1986) that various aromatic heterocyclic compounds yield conducting polymers. An article entitled "Polyaniline": Interconversion of Metallic and Insulating Forms published in Mol. Cryst. Liq. Cryst. 1985 Vol. 12, pp. 173–180 by MacDairmid et al describes polymers which may be processed to useful species herein.

An article entitled, "Enhanced Stability of Photoelectrodes With Electro Generated Polyaniline Films", by Noufi and Nozik, at Volume 129, No. 10, Page 2261 et seq. describes obtaining polyaniline on a platinum film while further describing the electrochemical behavior of such films in aqueous and non-aqueous solutions.

It is known from McMaster et al, U.S. Pat. No. 2,122,578, issued July 5, 1938, that lubricants and greases may be analyzed to determine their state of depreciation. McMaster et al describe as materials which are typically found in a crankcase as being the oil, acidic materials, water, fuel ends, inorganic solids, asphaltenes and blow-by carbon. McMaster discloses making conductivity measurements of the oil, but does not appear to do so on the basis of an ongoing, in-use basis of the oil nor is there any recognition by McMaster of measuring the acid content of the oil in the absence of the other ionic species which would also give rise to a conductivity measurement. In other words, McMaster et al cannot tell the difference between hydrogen ion concentration from an acid and the remaining ionic components.

Bzdula, in U.S. Pat. No. 4,434,233, issued Feb. 28, 1984 discloses mixing a sample of oil with an equal weight of distilled water to dissolve the ionic contaminants present in the oil. The contaminated water is then separated and its conductivity determined. Bzdula only discloses determining all of the ionic components and not hydrogen ion concentration. It is also observed that Bzdula cannot determine the conductivity or hydrogen ion concentration on an in situ basis.

Malmros, in U.S. Pat. No. 4,444,892, issued Apr. 24, 1984, describes a semi-conductor device for determining haptens, antigens and antibodies. In U.S. Pat. No. 4,560,534, issued Dec. 24, 1984 to Kung et al, it is disclosed that polymer-catalysts transducers may be obtained which are useful for the determination of glucose in whole blood. Of course, neither of the foregoing references relate to the determination of hydrogen ion concentration per se, or such a determination in the presence of a substantially non-aqueous medium.

Japanese Kokai Tokkyo Koho, 61 44,339, published Mar. 4, 1986 as application number 84/164,190, states that a polymer impregnated with a metal or a graphite particle may be used to determine the degree of deterioration of the oil according to the change in electrical resistance of the detector. A nickel powder dispersed in chloroprene is also disclosed in the foregoing reference. A device employing copper which dissolves in sulfur containing acids present in a lubricant is described in Canadian Patent 1,206,079 issued June 17, 1986 to Rolf.

Upson et al, in U.S. Pat. No. 4,237,194, issued Dec. 2, 1980, states that coating compositions useful in forming conductive layers comprising latex and water as a continuous phase, and as a dispersed phase, hydrophobic polymer particles having associated therewith a polyaniline salt semi-conductor may be prepared. The coating compositions are stated to be useful in forming anti-static layers for photographic elements.

Narrmann et al, in U.S. Pat. Nos. 4,401,545 and 4,532,188, issued respectively Aug. 30, 1983 and July 30, 1985, discuss the preparation of pyrrole polymers or copolymers. The materials of Narrmann et al are highly conductive organic polymers.

U.S. Pat. No. 4,543,402, issued to Traynor on Sept. 24, 1985, describes the preparation of pyrrole polymers and copolymers thereof which are suitable for compacting.

It, therefore, remains a desirable goal to obtain polymers which may be utilized to determine acidic hydrogen concentration in a substantially non-aqueous medium on an on-going basis. The present invention deals with such technology.

Throughout the specification and claims, percentages and ratios are by weight, temperatures are in degrees Celsius and pressures are in KPascals gauge unless otherwise indicated. To the extent that references cited herein are applicable, they are incorporated by reference.

SUMMARY OF THE INVENTION

This invention describes a device suitable for determining acidic hydrogen concentration of a substantially non-aqueous medium wherein the device includes an organic polymer capable of accepting protons, suitable means for exposing the organic polymer to the medium, means for transmitting an electric current to and from the organic polymer and suitable means for measuring differences in resistance through the organic polymer.

A further embodiment of the invention is a method for sensing the acidic hydrogen concentration of a substantially non-aqueous medium comprising obtaining an organic polymer, making a first measurement of the resistance of the organic polymer, exposing the medium to the organic polymer, then making a second measurement of the resistance of the organic polymer wherein the degree of acid hydrogen concentration of the substantially non-aqueous medium is determined. A further feature herein is a method for determining the acidic hydrogen ion concentration of a medium by:

(a) measuring the conductivity of an organic polymer;
(b) introducing the organic polymer to the medium;
(c) removing the organic polymer from the medium;
(d) determining the difference in resistance of the organic polymer;
(e) correlating the difference in resistance to the acidic hydrogen concentration in the medium. A useful polymer herein is a polyaniline polymer having a resistance of about $2.4 \times 10^6$ ohm/cm to $2.6 \times 10^6$ ohm/cm measured at 55° C.

DETAILED DESCRIPTION OF THE INVENTION

As previously described, this invention relates to sensing acidic hydrogen concentration in a substantially non-aqueous medium. The invention also relates to determining acidic hydrogen concentration in any medium, particularly those in which the acidic hydrogen concentration is relatively low. For purposes of exemplification, the term acidic hydrogen concentration is utilized to define both the actual hydrogen ion concentration of a medium and also that hydrogen ion concentration which is available to the sensing device. The invention herein is dependent upon an organic polymer and in conjunction with the definition given above, the organic polymer is a Lewis base with regard to its ability to accept acidic hydrogen species. That is, the organic polymers utilized herein are capable of taking in hydrogen species and thereby becoming conductive. The increase in conductivity may then be correlated to the increase in acidity or available acid species within the medium. It is also desirable herein that the medium not contain non-hydrogen ionic species in such amounts which allow a bridging across the polymer which would thereby give a higher conductivity reading and an apparent increase in the acidic hydrogen concentration in the medium. Thus the medium should not be more conductive than the organic polymer.

This invention is particularly useful in the area of non-aqueous mediums. For example, motor oils are typically formulated to contain basic materials such that the acid species which are formed due to decomposition of the oil are neutralized and the life of the oil is extended. It becomes particularly important to determine the point at which the oil should be changed. Thus, the idea is to allow the driver to determine the relative acidic hydrogen concentration on an ongoing basis while the vehicle is in operation. It is also desirable as the base reserve is replenished, either through an oil change or by the addition of oil that the acid sensor regenerate itself. The regeneration of the acid sensor described herein is accomplished by the alkaline materials utilized in the oil which then removes the acidic hydrogen species from the organic polymer. Thus, the conductivity of the organic polymer is lowered upon an oil change or the addition of oil to the engine. As the base reserve is again depleted through use, the conductivity of the organic polymer increases. While the organic polymer may eventually become contaminated with other ionic species, such is not substantially observed through one or two oil changes. Thus, the organic polymer is useful on a continuing and on-going basis and may be used through one or more oil changes. One mode of this invention comprises placing the oil sensor in an oil filter such that the sensor is replaced upon the recommended filter change interval for the vehicle. That is, most automotive manufacturers recommend that the oil filter be replaced at every other oil change.

The organic polymers as utilized herein may be any material which is itself substantially non-conducting or a semi-conductor. The organic polymer is intrinsically conductive in its protonated state.

The organic polymer in the deprotonated state must be capable of increasing its' intrinsic conductivity as it accepts acidic hydrogen from the surrounding medium. Thus the organic polymers are typically those materials capable of accepting an acidic hydrogen and which function as a Lewis base. It is also desirable that the organic polymer be a material such as is later described which has a relatively greater affinity for acidic hydrogen than does the surrounding medium.

The organic polymers and the acid sensing device of the present invention are also conveniently useful for flue gases. It has become important in recent years that the acid species in a flue gas (or any fluid stream) be determined. For instance, coal fired boilers generate substantial amounts of sulfur dioxide which has been related to the "acid rain" problem. As it is not precisely possible for the power plant operator to always know the sulfur content of the coal being burned, it becomes desirable to know when the sulfur content of the flue gas is higher than allowed amounts. The use of the acid sensor of the present invention in a flue gas stream is based on the presence of moisture and sulfur dioxide. The water and oxides of sulfur form sulfur containing acids in the flue gas and, thus, allow a measurement of the acidic hydrogen concentration of the gas. The measurement allows the operator of the plant to know when a lower sulfur content coal should be fed to the furnace.

Similarly, the presence of acid components such as nitric and sulfuric acid in the exhaust stream of a motor vehicle may be measured. When the acid content of the exhaust stream becomes too high, it is possible in some cases to adjust the vehicle operating conditions such that the acid content is lowered.

It is also possible, through the use of the organic polymers of the present invention, to measure the acidic hydrogen concentration when the hydrogen ions are in extremely low concentration. Thus, if it is desirable with distilled or de-ionized water to know the relative acidic hydrogen concentration, it is possible through placing the acid sensor, as described herein, in the water to determine the acidic hydrogen concentration. Of course, in this case, the water is a weaker a Lewis base than the deprotonated organic polymer. It is also possible to utilize the foregoing scenario and to remove the acid sensor from the de-ionized/distilled water and to make the measurement in the absence of the medium.

The following is a description of the formation of polypyrrole polymers which are further processed for use in the present invention.

The first organic polymer useful herein is a polymer of pyrrole or a copolymer of pyrrole.

The term "pyrrole" as used herein describes a material of the formula given below:

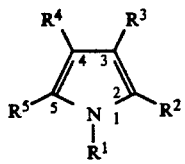

In the drawing above, $R^1$, $R^3$, and $R^4$ are all independently hydrogen or hydrocarbyl and $R^2$ and $R^5$ are always hydrogen. If $R^1$ is other than hydrogen, then a copolymerizable material containing hydrogen at the 1-position must also be employed as the organic polymer.

The term "pyrrole" thus includes materials which may be substituted at the three and/or four positions on the pyrrole molecule. A preferred material for use herein is the unsubstituted pyrrole, that is, the compound containing only carbon, nitrogen and hydrogen atoms. Copolymers of pyrrole include any material which may be condensed with pyrrole through the two positions which are alpha to the nitrogen atom in the pyrrole molecule thereby giving a structure favoring electron distribution throughout the molecule. Shown as compound (B) below is a repeating polymeric unit formed from pyrrole.

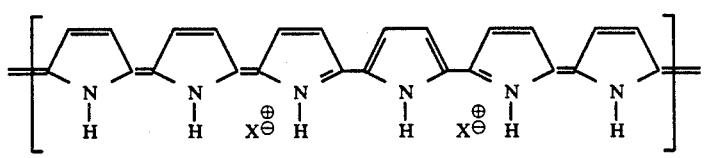

In B, and C, infra, the value $X^-$ is an anion such as the low mobility anion described herein.

Where a substituted pyrrole is intended, it is desirable that the substitution be of a non-electrophillic group. In particular, normal alkyls such as methyl, ethyl or propyl are useful. It is preferred, however, that the pyrrole be a non-substituted pyrrole. When substitution is present, it is preferred that the substitution be the beta, beta-disubstituted pyrrole.

Where copolymers of pyrrole are utilized, it is desirable that the pyrrole structure be the prominent material within the copolymer. Thus, the molar ratio of the pyrrole to the copolymer should be at least 1:1, and preferably greater than 2:1. A particularly preferred material for use as a copolymer with pyrrole is thiophene as shown in formula (C).

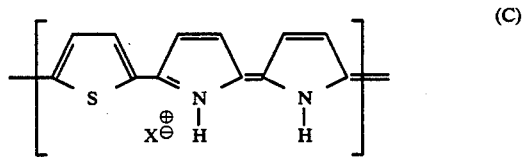

(C)

The surface area of the polymers as measured by the BET nitrogen method. The polymers obtained herein after deprotonation should have a surface area greater than 20 square meters per gram, preferably greater than 25 square meters per gram and most preferably greater than 50 square meters per gram. The upper limit on the surface area of the polymers is not particularly important.

Thus, the desirable effective range for the polymer of pyrrole or copolymer of pyrrole will be from about 20 square meters per gram to about 1000 square meters per gram, preferably from about 50 square meters per gram to 750 square meters per gram. Surface area of the polymer of pyrrole or copolymer of pyrrole is increased by treatment with base.

A method of obtaining the pyrrole for polymer is the use of a free radical mechanism to obtain the polypyrrole or copolymer of pyrrole. For instance, a material such as potassium persulfate ($K_2S_2O_8$) is used to generate a free radical of potassium persulfate. Other similar peroxygen systems may be used to polymerize the pyrrole. The persulfate is conveniently employed at a level of about 3 moles to 1 mole of the pyrrole. The reaction temperature for obtaining the pyrrole or co-polymer of pyrrole through the peroxygen method is at about 10° C. to about 50° C., preferably about 15° C. to about 30° C.

The peroxygen produced polymer of pyrrole or co-polymer of pyrrole is quite similar to the electrochemically produced polymer of pyrrole or co-polymer of pyrrole. A notable exception is that the peroxygen produced material gives a BET surface area, slightly greater for the polymer of pyrrole or co-polymer of pyrrole. It is further noted, however, that following deprotonation, the polymer of pyrrole or co-polymer of pyrrole obtained from the peroxygen method will not achieve as great a BET surface area as the deprotonated polymer of pyrrole or co-polymer of pyrrole obtained from the electrochemical process.

A preferred method of making the polymer of pyrrole or copolymer of pyrrole which is described in Bundesrepublik Deutschland Offenlegungsschrift 34 021 133 Al dated July 26, 1984, to Gerdes et al, herein incorporated by reference. The materials of Gerdes are electrically conducting polymers of pyrrole or copolymers of pyrrole. These materials are generally obtained by electropolymerization of pyrrole or a copolymerizable mixture containing pyrrole at an electronically conductive surface in an electrolytic bath.

The method of Gerdes et al comprises the steps of: (A) immersing an electronically conductive surface in an electrolytic bath comprising at least one liquid and at least one non-miscible liquid or gas or finely divided solid particles wherein the pyrrole or the copolymerizable mixture containing a pyrrole is one of the liquids or is dissolved in at least one of the liquids, and (B) passing an electric current through said bath at a voltage sufficient to electropolymerize the pyrrole or copolymerizable mixture containing a pyrrole at the electronically conductive surface. In a preferred embodiment the electrolytic bath comprises an aqueous mixture comprising pyrrole, or mixture of pyrrole and a copolymerizable monomer and water. The invention further provides for an electrochemical cell comprising polymeric electrode means, said polymeric electrode means being positive and/or negative and comprising electronically conducting polypyrrole or a co-polymer of pyrrole prepared in accordance with the foregoing method.

Further provided by Gerdes et al is a method of preparing electronically conducting polypyrrole or a co-polymer of pyrrole which comprises the steps of: (A) electropolymerizing a pyrrole or a copolymerizable mixture of a pyrrole at an electronically conductive surface in an electrolytic bath by (1) immersing an electronically conductive surface in an electrolytic bath which comprises (a) an aqueous dispersion of a pyrrole, or a mixture of said aqueous dispersion and at least one copolymerizable monomer or (b) a pyrrole or a mixture of a pyrrole and/or at least one copolymerizable monomer, water and a water-immiscible diluent, (2) agitating the bath, and (3) passing an electric current through said bath at a voltage sufficient to electropolymerize the pyrrole or pyrrole mixture and deposit the polymer or co-polymer on the electronically conductive surface, and (B) removing said polymer or co-polymer from the conductive surface. In a preferred embodiment of this method, the electrolytic bath comprises an aqueous mixture comprising pyrrole or a copolymerizable mixture of pyrrole, water, and one or more low mobility anions which are incorporated into the polypyrrole by electropolymerization and which anions are characterized by an average ionic transference number for said low mobility anions on reduction of less than about 0.1.

There is further described herein a method of preparing electronically conducting polypyrrole or a co-polymer of pyrrole which comprises electropolymerization of a pyrrole or a copolymerizable mixture containing a pyrrole at an electronically conductive surface in an electrolytic bath by (A) immersing an electronically conductive surface in an electrolytic bath comprising (i) a pyrrole or a mixture of a pyrrole with a copolymerizable monomer, (ii) one or more low mobility anions which are incorporated into the polypyrrole or co-polymer of pyrrole and which are characterized by an average ionic transference number for said low mobility anions during reduction of the polypyrrole or co-polymer of less than about 0.1, and (iii) an organic diluent, and (B) passing an electric current through said bath at a voltage sufficient to electropolymerize the pyrrole or copolymerizable mixture containing pyrrole at the electronically conductive surface. The polymer is formed in the oxidized state (black) which is electronically conductive.

The electronically conducting compositions of the present invention comprise either polypyrrole(s) or co-polymer(s) of pyrrole which may be obtained by (a) polymerizing mixtures of a pyrrole with other copolymerizable monomers or by (b) grafting a co-monomer(s) to a polypyrrole polymer or by (c) grafting a pyrrole monomer(s) to a preformed polymer based on a monomer other than pyrrole.

The pyrrole monomers which can be electropolymerized may be pyrrole or substituted pyrroles such as the C-substituted pyrroles as described more fully below. Homopolymers of these pyrroles, and preferably the homopolymers of unsubstituted pyrrole are included.

Co-polymers of a pyrrole can be prepared, for example, by polymerizing a mixture of pyrrole and one or more substituted pyrroles which may be substituted either on the nitrogen atom or at one or more of the ring carbon atoms in the beta position. Preferably, the substituent is a lower alkyl group containing from 1 to 7 carbon atoms, and it is more preferably a methyl group. Thus, for example, co-polymers of pyrrole and N-methylpyrrole or 3,4-dimethyl pyrrole can be prepared in accordance with the methods of the invention. Alternatively, pyrrole can be co-polymerized with other heterocyclic ring compounds including those containing nitrogen (e.g., pyridine, aniline, indole, etc.), furan and thiophene or with other aromatic or substituted aromatic compounds. It is necessary that the polymer not consist entirely of an N-substituted pyrrole as the homopolymers are not capable of being deprotonated.

The low mobility anions which are incorporated into the compositions to increase surface area may be either organic or inorganic anions. Examples of low mobility inorganic anions useful in the present invention include transition metal complexes such as ferricyanide, nitroprusside, iron/sulfur cluster compounds such as the redox centers of the rubredoxins and the ferredoxins, boron cluster compounds, cobalt hexacyanide, other transition metal cyanide complexes, nitroprusside complexes, and other transition metal oxy complexes or sulfides or chalcogenide complexes, e.g. $WO_4^-$, $MoO_4^-$, $Mo(CN)_8^{4-}$, $Fe_4S_4C_4H_{12}^-$, $CrO_4^-$, etc.

Preferably, the low mobility anions included in the compositions of the present invention are organic anions. Examples of organic anions include those derived from organic sulfates or sulfonates, and these may be alkyl, cycloalkyl, aryl, arylalkyl or alkaryl sulfates and sulfonates. The anions which are useful in the present invention may contain more than one anionic site, i.e., more than one ionizable group per molecule, e.g. more than one sulfonic acid group per molecule. The sulfonates and sulfates useful as the low mobility anions in the compositions of the present invention may be represented by the following formulas:

$R^1(SO_3)^{x-}$      Formula I $R^2(SO_3)^{x-}$      Formula II $R^1(OSO_3)^{x-}$      Formula III $R^2(OSO_3)^{x-}$      Formula IV $R^2_yT(SO_3)^{x-}$      Formula V $R^1_yT(SO_3)^{x-}$      Formula VI In the above formulas, $R^1$ is an aliphatic or an aliphatic substituted cycloaliphatic hydrocarbon or an essentially hydrocarbon group generally free from unsaturation and usually containing up to about 30 carbon atoms although it may be polymeric and contain more than 30 carbon atoms. When $R^1$ is aliphatic, it usually contains at least about 4 carbon atoms, and when $R^1$ is alkyl substituted cycloaliphatic, the alkyl substituents preferentially contain from 1 to 4 carbon atoms. Specific examples of $R^1$ include butyl, hexyl, octyl, lauryl, cetyl, octadecyl and groups derived from petroleum, saturated and unsaturated paraffin wax, and olefin polymers including polymerized mono-olefins and diolefins containing from 2 to about 8 carbon atoms per olefinic monomer unit. $R^1$ can also contain other substituents such as phenyl, cycloalkyl, hydroxy, mercapto, halo, nitro, amino, lower alkoxy, lower alkyl-mercapto, carbalkoxy, oxo or thio, or interrupting groups such as —NH—, —O—, —S—, but preferably its overall hydrocarbon character is retained.

$R^2$ generally is a hydrocarbon or essentially hydrocarbon group containing from 1 to about 30 carbon atoms, although it may be polymeric and contain more than 30 carbon atoms. $R^2$ is preferably an aliphatic hydrocarbon carbon group such as alkyl, alkenyl, or alkylaryl. $R^2$ also may contain substituents such as those enumerated above, including the above indicated interrupting groups, provided the essentially hydrocarbon character thereof is retained.

The group T in the above formulas V and VI is a cyclic nucleus which may be derived from an aromatic hydrocarbon such as benzene or from a heterocyclic compound such as pyridine. Ordinarily, T is an aromatic hydrocarbon nucleus and especially benzene. The subscript and superscript x represents the average number of ionized groups per molecule, The anion may contain additional sulfate or sulfonate groups which are not ionized but associated with some cationic species. In Formulas I through VI, x may have a value of up to 1000 or more when $R^1$ or $R^1$ is polymeric, but is preferably from 1 to 10, more preferably from 1 to 6, and generally is 1. The subscript y in Formulas V and VI is a number ranging from 1 to 5 and preferably is 1.

Anionic compounds containing the anions represented above by Formulas I through VI are available commercially or can be prepared readily by techniques known in the art. Examples are salts with alkali or alkaline earth metals, or ammonium salts.

Examples of sulfonates useful in the invention include the anions of the following acids; hexyl sulfonic acid, octyl sulfonic acid, dodecyl sulfonic acid, octyldecyl sulfonic acid, lauryl sulfonic acid, mahogany sulfonic acid, paraffin wax sulfonic acid, benzene sulfonic acid, naphthalene sulfonic acid, lauryl cyclohexyl sulfonic acid, dodecyl benzene sulfonic acid; polyethylene sulfonic acids of various molecular weights; polystyrene sulfonic acids of various molecular weights, etc. Styrene maleic anhydride co-polymers bearing sulfonate groups on the rings or styrene maleic anhydride co-polymers which have been partially or fully converted to the corresponding imide sulfonates are also useful anionic species in the invention; such materials are derived from styrene maleic anhydride co-polymers typically having inherent viscosity of about 0.06 to about 1, preferably about 0.06 to about 0.3 dl $g^{-1}$ measured at 30° C. in acetone, 0.4–1 g $dl^{-1}$.

A preferred embodiment includes anions derived from aliphatic compounds containing two sulfonic acid groups and may be represented by the formula $(CH_2)_n(SO_3)_2^{2-}$      Formula VII wherein n is an integer from about 2 to 20 or more and preferably about 2 to 12. These disulfonic acid salts can be prepared by techniques known in the art such as by the reaction of alkylene dihalides with sodium sulfite. Specific examples of such compounds include the salts of ethane disulfonic acid, 1,4-butane disulfonic acid, 1,5-pentane disulfonic acid, 1,6- hexane disulfonic acid, 1,8-octane disulfonic acid and 1,10-decane disulfonic acid.

Examples of sulfates which are useful include alkyl sulfates such as lauryl sulfate; and polyethylene sulfates of various molecular weights.

Another class of sulfates which are useful as the low mobility anions are polysulfates polyhydroxy compounds. Such compounds can be obtained by reacting polyhydroxy compounds with an appropriate reagent such as chlorosulfonic acid thereby converting one or more of the hydroxy groups to sulfate groups. Examples of polyhydroxy compounds which can be used to prepare such polysulfates include pentaerythritol, mannitol, trimethylolpropane, dipentaerythritol, etc. As mentioned, one or more of the hydroxy groups in these polyhydroxy compounds can be sulfated to produce a variety of products. Ammonium sulfates can be prepared directly from polyhydroxy compounds by reaction with an aminosulfonic acid in the presence of a diluent such as dimethyl formamide.

Amido, and preferably acrylamido alkane sulfonic acid anions can be used in the compositions of the invention. Specific examples of such anions include: 2,2-bisacrylamido-1,1,-dimethylethanesulfonic acid anion; 2-acrylamido-2-methyl propane sulfonic acid anion; and poly(2-acrylamido-2-methyl) propane sulfonic acid sodium salt of various molecular weights.

The low mobility anions included may also be derived from pentavalent phosphorous compounds. Examples of such phosphorous compounds are phosphates, phosphonates and phosphinates. The phosphorous compounds useful as the low mobility anions may be represented by the following formulas:

$$(R^3(X^1)_aP(X^4)(X^3)[(X^2)_bR^4])^{-1} \quad \text{Formula VIII}$$

$$[R^3(X^1)_aP(X^4)(X^2)(X^1)]^{-2} \quad \text{Formula IX}$$

$$[R^4(X^1)_aP(X^4)(X^2)(X^3)]^{-2} \quad \text{Formula X}$$

$$R^3[(X^1)_a(X^4)(X^3)P(X^2)_bR^4]_z^{-z} \quad \text{Formula XI}$$

$$R^4[(X^1)_a(X^4)(X^3)P(X^2)_bR^3]_z^{-z} \quad \text{Formula XII}$$

$$R^3[(X^1)_aP(X^2)(X^3)(X^4)]_z^{-2z} \quad \text{Formula XIII}$$

$$R^4[(X^1)_aP(X^2)(X^3)(X^4)]_z^{-2z} \quad \text{Formula XIV}$$

In the above formulas $R^3$ is $R^1$ or $R^1yT$ as defined above, or can be hydrogen, an alkali metal (e.g., lithium, sodium, potassium, etc.) or an alkaline-earth metal (e.g., calcium, magnesium, etc.). $R^4$ is $R^2$ or $R^2yT$, as defined above, or can be hydrogen, an alkali metal (e.g., lithium, sodium, potassium, etc.) or an alkaline earth metal (e.g., calcium, magnesium, etc.). Each of $X^1$, $X^2$, $X^3$ and $X^4$ is oxygen or sulfur (e.g., a phosphorus double bond); and each a and b is 0 or 1. The subscript and superscript z represents the average number of ionized groups per molecule. In Formulas XI through XIV, z may be a value of up to 1000 or more when $R^1$ or $R^2$ is polymeric, but is preferably from 1 to 10, more preferably from 1 to 4, and generally is 1. Thus, it will be appreciated that the pentavalent phosphorous compounds may be for example, organophosphoric, phosphonic or phosphinic compounds including the acids, alkali metal salts and alkaline-earth metal salts thereof, or a thio analog of any of these.

It also has been discovered that when the electropolymerization of pyrrole or polymerizable mixtures of such as pyrrole is carried out using either an aqueous medium or a multi-phase system as described below, the presence of a plasticizer such as polyethylene glycol confers mechanical strength and flexibility to the polymeric compositions obtained. Moreover, when polyethylene glycol of various molecular weights is added to electrolytic baths of the invention, the morphology of the polymeric composition obtained generally can be modified by varying the molecular weight of the glycol added.

The amount of plasticizer included in the electrolytic bath may vary over a wide range, particularly if the low mobility anion also functions as a plasticizer. Generally, however, the electrolytic bath compositions will contain less than about 75% of plasticizer and preferably, less than about 25% by weight of the plasticizer based on the total weight of the bath composition.

Surface active agents, also variously referred to as wetting agents or emulsifying agents, may be included in the compositions and in the electrolytic baths. The surface active agent may be hydrophilic or hydrophobic. Typically, the surfactant is a hydrophilic surfactant, and generally, has an HLB (hydrophilic-lipophilic balance) in the range of about 10 to about 20.

The surfactant can be of the cationic, anionic, nonionic or amphoteric type. Many such surfactants of each type are known to the art. See, for example, McCutcheon's "Detergents and Emulsifiers", 1978, North American Edition, published by McCutcheon's Division, MC Publishing Corporation, Glen Rock, N.J., U.S.A., particularly pages 17–33.

The electronically conducting polypyrrole or co-polymers of pyrrole are prepared by electropolymerization of a pyrrole or a co-polymerizable mixture containing a pyrrole at an electronically conductive surface in an electrolytic bath. The electrolytic bath contains a pyrrole or mixture of pyrrole and copolymerizable monomer, at least one electrolyte salt which includes an anion which will be incorporated into polymer upon formation and at least one liquid in which the pyrrole (and/or co-polymer) and electrolyte salt together have some finite solubility. The bath may additionally contain a second non-miscible liquid or a gas or finely divided solid particles or combinations thereof. In one embodiment, the electrolytic bath comprises a pyrrole or co-polymerizable mixture of pyrrole and water. In another embodiment, the electrolytic bath comprises the pyrrole or co-polymerizable mixture of pyrrole and an organic diluent. In yet another embodiment, the electrolytic bath comprises the pyrrole or co-polymerizable mixture containing pyrrole, water, and a non-miscible liquid such as an organic diluent. The last embodiment wherein the bath contains water and a non-miscible organic diluent, hereinafter referred to as the two-phase system, is useful in preparing compositions which may be characterized as being porous and having very high surface areas.

The electropolymerization of a pyrrole or a co-polymerizable mixture containing a pyrrole utilizing a two-phase system such as water and an organic diluent comprises the steps of:

A. immersing an electronically conductive surface in an electrolytic bath comprising at least one liquid and at least one non-miscible liquid wherein the pyrrole or co-polymerizable mixture is one of the liquids or is dissolved in at least one of the liquids and B. passing an electric current through said bath at a voltage sufficient to electropolymerize the pyrrole or co-polymerizable mixture containing a pyrrole at the electronically conductive surface. Preferably, one of the liquids is water and the non-miscible liquid is an organic diluent. Examples of organic diluents include organic hydrocarbons such as aliphatic or aromatic hydrocarbons, halogenated aliphatic or aromatic compounds, etc. specific examples include mineral spirits, hexane, heptane, toluene, xylene, 1,2-dichloroethane, dichloromethane, carbon tetra-chloride, and chlorobenzene. of the pyrrole or co-polymerizable mixture containing pyrrole in the electrolytic bath may vary over a wide range although the total amount must exceed the amount necessary to form the total amount of polymer desired. The amount of the pyrrole dissolved in the electrolyte solution component(s) of the electrolytic bath must be enough to permit a reasonable rate of reaction. The amount will usually vary from about $10^{-3}$ molar up to saturation of the electrolyte(s). The amount of electrolyte salt in the electrolytic bath must be sufficient to both conduct the current desired and provide sufficient anionic species for incorporation into the polymer for the purpose of charge neutralization. Typical concentrations are from $10^{-2}$ molar up to saturation of the bath.

Only a small amount of the stabilizer is necessary for the purpose. It may be as little as 0.01 part and seldom exceeds 2 parts per 100 parts by weight of the electrolytic bath. In most instances it is within the range from 0.1 to 3 part per 100 parts of the bath.

As mentioned, the electropolymerization process can be carried out in an organic diluent and more particularly in an organic phase containing less than about 3% and more preferably less than about 1% of water. Examples of organic diluents include polyols, organic carbonates, ethers, nitriles, etc. It is essential that the solvent does not undergo competitive oxidation during the electropolymerization and thus interfere with the polymerization or substantially reduce the current efficiency of the polymerization process.

The electropolymerization of pyrroles from aqueous media, by either a single-phase aqueous system or a multi-phase aqueous system is possible. Many of the advantages of using aqueous systems are apparent including, reduced costs, availability and easy purification of water, the ability to utilize a wide range of ionic materials as electrolyte salts in water, the ability to utilize high concentrations of ionic species thus permitting high electrochemical currents and high polymer formation rates. Under controlled conditions, intact homogeneous films of polypyrroles can be formed on a variety of substrates in aqueous media. Thicknesses range from less than 100 Angstroms to a few millimeters for more dense materials. In some instances, current density has an effect on the morphology. The morphology of the electropolymerized compositions can be further modified by the use of the additives already discussed.

It has been observed that improved results are obtained when the electroplating bath is thoroughly agitated during the electropolymerization of the monomers. Agitation can be accomplished by any known technique including vigorous stirring with paddle mixers, magnetic stirrers, ultrasonics, vibration or by bubbling gases through the bath to provide sufficient agitation (including gases generated at the counter-electrode). Electropolymerization is accomplished by passing an electric current through the bath at a voltage which is sufficient to electropolymerize the pyrrole or co-polymerizable mixture containing a pyrrole at an electronically conductive surface immersed in the electrolytic bath. The electric current may be a continuous electric current or a varying electric current such as a pulse current. Generally, the electric current is direct current although in some instances alternating current may be useful.

The voltage at the anode should be sufficient to oxidize monomer without producing significant changes in the bath, such as degradation of a bath component, which would adversely affect the polymerization. Generally, current densities of up to two amperes per square centimeter may be used, but preferably, current densities not exceeding 500 milliamperes per square centimeter are utilized. The current density will be less than 250 and more generally, less than 100 milliamps per square centimeter.

At the above current densities, the pyrrole or copolymerizable mixture of a pyrrole is electropolymerized at the electronically conductive surface. Depending upon the specific ingredients in the plating bath, the electropolymerizable polypyrrole may either form as a powder at the electronically conductive surface and fall into and be dispersed in the electrolytic bath, or alternatively, be deposited on the conductive surface. The deposit may be in the form of a film which is either smooth and dense or irregular with less than the bulk or theoretical density. Bulk or theoretical density of the polymers is the density of continuous, pure polymer containing no voids, pores, cavities or inclusions. The bulk or theoretical density can usually be determined by floatation methods. Examples of irregular deposits include porous films, powders, dendriform materials, etc.

The nature of the cation(s) as well as that of the anion(s) present in the electrolytic bath affects the electropolymerization. The morphology of the deposit on the electronically conductive substrate can be controlled and modified by the incorporation in the electrolytic bath of various complexing agents for the ionic constituents of the electrolyte. Examples of materials which function as growth regulators when incorporated into the electrolytic bath include the above-discussed non-ionic plasticizers (e.g. polyalkylene glycol such as polyethylene glycol), cryptands, and commercially available crown ethers such as 12-Crown-4, 15-Crown-5, and 18-Crown-6 available from Aldrich Chemical Co.

The temperature of the electrolytic bath during the electropolymerization process is generally maintained between about 15° C. to about 50° C., although polymerization proceeds over a much wider temperature range. The reaction is conducted at or about room temperature and preferably under thermostatted conditions.

A variety of electronically conductive substrates that do not undergo competitive oxidation during the electropolymerization can be utilized in the process of the invention. Not all types of metals can be used with the entire range of bath formulations. For example, although steel surfaces are useful for electropolymerizing pyrrole in the presence of sodium lauryl sulfate and water, the electrolytic bath containing pentaerythrityl tetrasulfate and water will not deposit a satisfactory film on steel, but deposits a satisfactory coating on nickel substrates. The choice of particular substrate material can be readily determined by those skilled in the art, with a minimum of experimentation. The size and shape of the substrate utilized in the process of the invention will vary depending upon the type of cell in which the electropolymerization process is conducted and on the desired form of the polymer. For example, when flat films are desired, the substrate will be in shape of a flat panel in a parallel plate cell.

A preferred embodiment provides for a rotating cylindrical anode or a moving belt anode from which the polymer is removed in a continuous process. The polymer can also be collected or stripped from a stationary electrode in a continuous manner.

The time required to produce a given quantity or thickness of polymer will depend upon several factors, including the current density, bath temperature, size or physical dimensions of the electronically conductive surface and the temperature of the electrolytic bath. Moreover, the specific type of morphology desired will be an important consideration when selecting the values of the process variables such as temperature, current density, time of coating, voltage, etc.

One of the advantages of the process, particularly with the aqueous systems, is the ability to produce films of controlled thickness over a wide range of thicknesses, and in particular, films having thicknesses greater than 250 micrometers, and in particular, thicknesses between a range of 0.5 mm. to 2 cm. Many prior art processes have not been developed to the level required to produce anything but thin films (200 micrometers or less).

In the general process of the invention, the electronically conductive surfaces are introduced into the electrolytic bath and connected to a current source. The polymer is formed at the anode. The counterelectrode may consist of the bath tank or a separate conductive surface(s) may be introduced into the electrolytic bath.

The bath may have a separate compartment for the secondary electrode but the one compartment configuration is preferred.

When the electropolymerization process is completed, the substrate is removed from the electrolytic bath, and the electropolymerized material is mechanically stripped from the surface. This polymer may be washed with water and with various non-aqueous solvents (e.g., ethers, liquid hydrocarbons, etc.) to remove any undesirable deposits contained on or in the material. If the deposited material has not been fully dried, this can be achieved, if desired, by heating the polymer at elevated temperatures, preferably under vacuum. The particular temperatures will depend upon the nature of the pyrrole or co-polymerizable mixture of pyrroles utilized in the process, but will generally be less than 250° C. and preferably below 100° C.

The following examples illustrate the process of obtaining the polymer of pyrrole or copolymers of pyrrole:

Unless otherwise indicated, in the following examples, electropolymerizations are conducted at 2 amperes for 30 minutes using a Hanovia arc-lamp power supply controlled with a Variac. Agitation is accomplished with a horizontal perforated glass disk mounted on the bottom of a stirring rod (about 1 to 2 cm from the bottom of the bath) and rapidly vibrated up and down with a Vibro-Mixer (Model El, supplied by A.G. Fur Chemie-Apparatebau Mannedorf-Zurich). The temperature is controlled with an ice bath. Both electrodes are 15×7.5×0.05 cm panels of steel (AISI No. 10/10) in parallel plate configuration that have been degreased with toluene. The surface area (one side) of each electrode immersed in the bath is 70 $^2$ and the distance between the electrodes is 5.5 cm. The polyethylene glycol used in some of the examples has an average molecular weight of about 15–20,000. The bath is exposed to the atmosphere. The descriptions of the polymer films of the following examples do not cover edge effects. These effects produce irregularities which rarely affect more than five percent of the total mass of the film. Other useable forms of pyrrole polymers include those of Naarmann described infra.

EXAMPLE 1

In this example, the following components are utilized:

|  | Grams |
| --- | --- |
| Pyrrole | 40 |
| Sodium Lauryl Sulfate | 40 |
| Polyethylene Glycol | 20 |
| Distilled Water | 1600 |
| Heptane | 200 (ml.) |

The above first four ingredients are mixed in a container until homogeneous, and 375 ml. of this mixture is added to the 10.8×8.9×5.7 cm. reaction vessel. Two steel panel electrodes are put into place. Heptane (50 ml.) is added, and agitation is accomplished mechanically with a Vibro Mixer.

Four films are separately prepared at 2 amperes utilizing a reaction time of 30 minutes. The temperature is controlled with an ice bath and is initially 21° C. and rises to a temperature of about 34°-37° C. during the reaction. The current is maintained at 2 amperes, but the voltage changes from about 60 to about 40 volts during the course of the reaction. The electrolyte side of each film has a few irregularities in the form of dendriform projections (about 1 millimeter) and these projections are removed by light abrasion before stripping the films from the electrode surfaces. Each film is rinsed thoroughly in distilled water and in heptane.

Two of the films are fully dried in a vacuum oven at 50° C. for 24 hours. The cleaned films obtained in this manner appear to comprise 3 layers. The first layer which is the layer closest to the steel panel is smooth and continuous. The second layer adjacent to the smooth layer is a uniformly porous material and the third layer adjacent to the second layer is denser and less porous.

EXAMPLE 2

A mixture of 5 grams of pyrrole, 1 gram of sodium ethane disulfonate, 2 grams of polyethylene glycol and 200 grams of water is prepared and added to an 8×7×4.5 cm reaction vessel. The cathode is a 15×5×0.025 cm piece of Precision brand shim steel (a product of Precision identified as NIDA/SIDA 1613D Al). The anode is a 10×5×0.05 cm Nickel 200 panel. (Nickel 200 is a product of Inco identified as a high purity nickel.) The surface area (one side) of each electrode immersed in the bath is about 40 cm$^2$. Toluene (20 ml.) is added and the mixture agitated using a Vibro-Mixer. The electropolymerization reaction is conducted for 15 minutes at a constant current of 0.5 amperes at a potential of about 17 volts. The film formed on the electrode is removed and observed to be a relatively porous uniform film of about 0.3 to 0.4 mm in thickness.

EXAMPLE 3

A mixture of 20 grams of pyrrole, 4 grams of pentaerythrityl tetrahydrogensulfate, 4 grams of polyethylene glycol and 800 grams of water is prepared and mixed until homogeneous. A volume of 375 ml. is added to a 5.7×8.9×10.8 cm reaction vessel, and 50 ml. of dichloromethane also is added to the vessel. In this example, a panel of steel (AISI No. 10/10) (15×7.5×0.05 cm) is used as the cathode, and a Nickel 200 sheet (14.2×7.6×0.025 cm) is used as the anode. The electropolymerization is carried out in a normal manner over a period of 15 minutes while maintaining a current of 2 amperes. A porous mass of approximately 1 cm in thickness with a low density (less than 0.1 g cm$^{-3}$) is obtained; this porous mass is electronically conducting.

EXAMPLE 4

A mixture of 20 grams of pyrrole, 10 grams of sodium-1,10-decane disulfonate, 10 grams of polyethylene glycol and 800 parts of water is prepared, and 375 ml. added to each of two reaction vessels. Heptane, (50 ml) is added to each reaction vessel, and the electropolymerization carried out in the normal manner at a current of 2 amperes. The electropolymerization in the first reaction vessel is terminated after 5 minutes yielding a thin black electronically conductive film covered with small dendriform projections of about 1 mm. in height.

The electropolymerization reaction in the second vessel is carried out for 39 minutes yielding a thicker base film covered with small dendriform projections of approximately the same dimensions as for the previous film.

EXAMPLE 5

A mixture of 10 grams of pyrrole, 10 grams of sodium lauryl sulfate and 0.5 grams of polyethylene glycol is prepared and added to the reaction vessel. In this example, both electrodes are steel panels and agitation is by a Vibro Mixer. The electropolymerization reaction is conducted for 20 minutes at a current of 2 amperes. A thick rather uniform coating is deposited on the anode and the coating is covered with small dendriform shapes which are easily removed by light abrasion.

EXAMPLE 6

The procedure of Example 5 is repeated except that 50 ml of heptane is added to the mixture in the reaction vessel, and the electropolymerization is conducted for five minutes at 2 amperes. The film prepared in this manner is more porous than the material obtained from the procedure of Example 5 and is covered with dendriform shapes.

EXAMPLE 7

Pentaerythrityl tetrasulfate ammonium salt is prepared from pentaerythritol and sulfamic acid in N,N,-dimethylformamide. A mixture of 5 grams of pyrrole and 5 grams of the ammonium salt in 200ml. water is prepared and electropolymerized in a $8\times 7\times 4.5$ cm reaction vessel wherein the cathode is a $15\times 5\times 0.025$ cm nickel sheet. About 40 $cm^2$ of the nickel sheet is immersed in the bath. The distance between electrodes is 4.5 centimeters. Electropolymerization is conducted at a current of 0.3 amperes for a period of 10 minutes yielding a black electronically conducting film characterized by a somewhat rough surface on the solution side of the film.

EXAMPLE 8

The procedure of Example 7 is repeated except that 2 grams of polyethylene glycol is included in the mixture contained in the reaction vessel. The black electronically conducting film obtained in this manner is more uniform and smoother on the solution side than the film obtained in Example 7.

EXAMPLE 9

Mannityl hexasulfate ammonium salt is prepared from mannitol and sulfamic acid in dimethylformamide. A mixture of 5 grams of pyrrole and 1 gram of this ammonium salt is dissolved in 200 ml. of water. Utilizing the apparatus described in Example 7, the polymerization is carried out at a current of about 0.4 amperes over a period of 20 minutes. The product is a black electronically conducting film which is shiny on the substrate side and rough on the solution side.

EXAMPLE 10

The procedure of Example 9 is repeated except that 2 grams of polyethylene glycol is added to the mixture in the reaction vessel. A more uniform film is obtained in this example which is much smoother on the solution side.

EXAMPLE 11

A mixture of 15 grams of pyrrole in 500 grams of water is prepared, and a second mixture of 10 grams of potassium ferricyanide and 5 grams of polyethylene glycol is prepared in 400 ml. of water. The two solutions are mixed together and shaken. Approximately 450ml. of the mixture is poured into the $10.8\times 8.9\times 5.7$ cm reaction vessel. The electrodes used in this example are both steel panels. The electropolymerization is conducted at 5 amperes. At the start of the reaction, the temperature is 23° C. and the voltage is 22 volts. During the electropolymerization reaction, the temperature is stabilized at 31°–32° C. with an ice bath. At this temperature, 20 volts is required to maintain a current of 5 amperes. The distance between electrodes is 5.5 cm. The electropolymerization reaction is conducted for 40 minutes. The polymer is then removed from the anode. This film is 0.8 mm. thick, black and electronically conducting. The film is smooth on both sides although smoother on the substrate side.

EXAMPLE 12

The procedure of Example 11 is repeated except that the 15,000–20,000 molecular weight polyethylene glycol is replaced by an equivalent weight of Carbowax 4000 (a product of Union Carbide identified as 4,000 molecular weight polyethylene glycol). The electropolymerization reaction is conducted at 5 amperes current and about 20 volts are required to maintain this current throughout the 40 minute reaction period. The temperature of the bath ranges from 22° to 32° C. The polymer is removed from the electrode, and the film obtained in this manner is black and electronically conducting. The substrate side is smooth while the solution side is covered with dendriform structures.

EXAMPLE 13

A mixture of 2 grams of pyrrole, 0.4 grams of a 50% aqueous solution of the sodium salt of 2-acrylamido-2-methylpropanesulfonic acid and 100 ml. of water is prepared and mixed until homogeneous. In this example, the cathode of the reaction vessel is a platinum strip $(0.5\times 3$ cm.) and the anode is a gold surface $(2\times 4$ cm) with about 4 $cm^2$ immersed in the bath. The electrodes are rinsed with distilled water prior to use. The electropolymerization in this example is carried out using a Hewlett Packard power supply/amplifier Model 6824A. The electropolymerization reaction is conducted at a current of 24 milliamps and at a voltage of 15 volts for a period of 2 minutes. A thin black electronically conductive film is deposited on the gold surface.

EXAMPLE 14

The procedure of Example 13 is repeated except that the electrolyte salt utilized in poly(2-acrylamido-2-methylpropanesulfonic acid sodium salt having an inherent viscosity of 0.1 dl. g.⁻(measured in 0.5 N NaCl at 30° C.). The electropolymerization is conducted at 30 milliamps at 20 volts for a period of 2 minutes. A smooth thin glossy black electronically conducting film is deposited on the gold surface.

EXAMPLE 15

A mixture of 20 grams of pyrrole, 20 grams of sodium lauryl sulfate, 10 grams of polyethylene glycol and 800 grams of water is prepared, and 375 ml. of this mixture 800 grams of water is prepared, and 375 ml. of this mixture is added to the $10.8\times 8.9\times 5.7$ cm reaction vessel. Heptane (50 ml) for each experiment is then added to the reaction vessel, and agitation is accomplished with a rapidly vibrating glass disk. The temperature is controlled with an ice bath. In this example, the electropolymerization is carried out using a current of 2 amperes. The reaction time is 30 minutes and the reaction temperature ranges from 20°-38° C. The polymer formed on the anode is removed and cleaned by washing several times in distilled water. The film prepared in this manner comprises a very thin base layer next to the substrate, a uniformly porous layer adjacent the base layer and a denser wrinkled less porous layer on the electrolyte side. The polymer layer is removed from the electrode and a 4×1 cm strip is cut from the film and its thin base layer is removed. The rest of the film is broken into pieces and rinsed several times with distilled water along with the strip. The pieces and the strip are then rinsed further in a Soxhlet extractor using distilled water for 15 hours (about 40 extractions). The materials are then dried in a vacuum oven at 80° C. for 29 hours. This polymer is electronically conducting and can be ground dry to a porous powder which is easily cold pressed without any additives into various shapes as desired. The shapes obtained in this manner are also electronically conducting.

EXAMPLE 16

The procedure of Example 15 is repeated except that the mixture contains only 7.5 grams of polyethylene glycol. The electropolymerization of the mixture results in a thinner, denser film than obtained in Example 15. The film also does not appear to be as flexible and the corresponding powder does not cold press as well as the powder obtained in Example 15.

EXAMPLE 17

The procedure of Example 15 is repeated except that the mixture contains only 5 grams of polyethylene glycol. The film obtained in this manner is electronically conductive, is thinner than the film obtained in Example 16 and is less uniform.

EXAMPLE 18

An electrolyte bath is prepared comprising 1 g of phenyl phosphonic acid and 2 g of pyrrole in 100 g of water. The electropolymerization is carried out in the unstirred bath on a gold strip of dimensions 3 cm×0.5 cm. The gold strip is immersed to a depth of 1 cm. A platinum counter-electrode is employed and a current of 1 milliampere is maintained for 300 seconds. The product is a black electronically conducting film.

EXAMPLE 19

A mixture of 40 grams of pyrrole, 40 grams of sodium lauryl sulfate, 15 grams of polyethylene glycol and 1,600 grams of water is agitated until homogeneous, and 1200 ml is added to a 8.25×14×19 cm plastic reaction vessel. Both electrodes are 14×19×0.1 cm panels of steel (AISI No. 10/10 steel plate degreased with toluene. Heptane (150 ml) is added and agitation is accomplished with a Vibro Mixer. The surface area of the anode covered with polymer is about 250 cm$^2$. The electropolymerization reaction is conducted for a period of one hour at a current of about 4 amperes D.C. The product is removed from the anode and partially pulverized by hand while washing with distilled water. After further washing (Soxhlet extraction with distilled water) and drying, (vacuum oven, 85° C., 20 hr.) the polymer was pulverized further with a mortar and pestal. In this manner, fine black electronically conducting powder is obtained.

The powder obtained in this example can be cold pressed at room temperature in the dry state without any additives, and the pressed electrodes obtained in this manner exhibit improved electronic conductivity over the dried electropolymerized films. The density of the electropolymerized film is about 0.2 g cm$^{-3}$ whereas the density of the pressed electrode is about 0.8 g cm$^{-3}$.

EXAMPLE 20

The procedure of Example 19 is repeated except that the power source is a simple full wave rectifier (12 amp rating) controlled with a Variac. The voltage requirements are essentially identical to those of Example 19.

The electronically conductive polymers of co-polymers prepared above are useful, for example, for electrodes in electrochemical cells (e.g., as electrodes in batteries, both primary and secondary batteries); as coatings for photocells to inhibit photo-corrosion or corrosion processes; for catalytic electrodes; for electric conductors; for conductive substrates and/or binders and mixtures for composite electrodes; for switching devices; and as durable or corrosion resistant electropolymerized coatings. The electronically conductive polymers are also useful in solid state applications (e.g., in the formation of junctions) and/or for photovoltaic and photoelectrochemical devices and as reversible electrode materials in electrochemical cells and batteries.

The polymer of pyrrole or copolymer of pyrrole when obtained from electrodeposition is conveniently removed from the electrode by scraping or mild agitation. Where the free radical method is used to generate the polymer of pyrrole or copolymer of pyrrole, the mixture may be stripped of excess solvent, reactant and other materials and thereafter treated with the strong base in order to substantially increase the surface area. Of course, where the electrochemical method is utilized, the scraped material may be washed, otherwise prepared and thereafter treated in a suitable solvent with the strong base to remove the counter anion thereby substantially increasing the surface area.

The next aspect of the present invention discusses the deprotonation of the polymer of pyrrole or co-polymer of pyrrole. It will be observed that when using the electrochemical method, an anion of an organic material, typically, a lauryl sulfate anion will be associated with the polymer of pyrrole or co-polymer of pyrrole. When the peroxygen method is employed, an anion such as $KSO_4^-$ is intimately associated with the polymer of pyrrole or co-polymer of pyrrole.

It has been determined that the anion associated with the polymer of pyrrole or co-polymer of pyrrole may be removed utilizing a strong base. By a strong base, it is intended to exclude such weak materials which cannot effectively remove substantially all of the anion associated with the polymer of pyrrole or co-polymer of pyrrole. Suitable materials which may be utilized to remove the anion include materials such as the alkali metal and alkaline earth metal hydroxides, the alkali metal and alkaline earth metal alkoxides, and various amine bases. The alkali metal hydroxide of choice is sodium hydroxide. However, potassium hydroxide, lithium hydroxide or even cesium hydroxide may be utilized to remove the anion from the polymer of pyrrole or co-polymer of pyrrole. Among the alkaline earth metal hydroxide which may be utilized, it is suggested that calcium hydroxide is most convenient from a cost effective standpoint. However, material such as magnesium hydroxide may also be utilized effectively to remove the anion from the polymer of pyrrole or co-polymer of pyrrole.

The alkoxides utilizable herein are any of the conventional alkoxides such as sodium or potassium methoxide. Of course, the methoxides are typically utilized in mixture with the alcohol corresponding to the alkoxide moiety. The solvent utilizable for removing the anion when a water-soluble base is utilized is conveniently water. It is, of course, however, possible to use mixtures of various solvents to obtain a greater effect in removal of the anion.

A concomitant effect of removing the anion from the polymer of pyrrole or co-polymer of pyrrole is to remove the acidic proton which is associated with a charged pyrrole ring. As the polymer of pyrrole or co-polymer of pyrrole is now deficient in a proton, the corresponding nitrogen atom on the polymer has an unshared electron pair. The deprotonated polymer then becomes a Lewis base thereby making it possible to associate any of several Lewis acids or Broensted acids species within the polymer matrix.

The polymer matrix is also useful in that the unshared pair of electrons on a nitrogen atom within the polymer of pyrrole or co-polymer of pyrrole may be covalently bonded to another species to provide an additional catalytic usage of the deprotonated polymer of pyrrole or co-polymer of pyrrole.

It is also possible to reprotonate the deprotonated polymer of pyrrole or copolymer of pyrrole. A more responsive system is obtained by subsequently treating the polymer or copolymer to a specific degree of protonation. That is, the polymer of pyrrole or copolymer of pyrrole, following its electrochemical production with a material such as sodium lauryl sulfate included therein provides a material having a far greater surface area following removal of the lauryl sulfate anions. When reprotonating the polymer of pyrrole or copolymer of pyrrole with a material such as a mineral acid, it is possible to thereafter obtain a material having an extremely high surface area which is a protonated polymer of pyrrole or copolymer of pyrrole.

Suitable materials which may be used to reprotonate the polymer of pyrrole or copolymer of pyrrole include any of the non-oxidative acids. Thus, mineral acids such as phosphoric, sulfuric or hydrochloric acids are suitable to reprotonate the polymer of pyrrole or copolymer of pyrrole. Organic acids such as methane sulfonic acid may also be used to reprotonate the polymer of pyrrole or copolymer of pyrrole. In any event, the amount of acid employed is usually a slight excess over that required to completely associate a proton with the unpaired electron on the nitrogen atom. The slight excess of the acid is utilized for convenience considering the cost of polymer of pyrrole or copolymer of pyrrole.

The degree with which the polymer of pyrrole or copolymer of pyrrole is reprotonated is also a matter of choice directed to the eventual utility of the polymer of pyrrole or copolymer of pyrrole. Accordingly, any acid may be used to reprotonate the polymer of pyrrole or copolymer of pyrrole providing it does not substantially destroy the polymer backbone.

The following are examples of the deprotonation of pyrrole polymers.

EXAMPLE A

A sample of a polymer of pyrrole corresponding to unsubstituted pyrrole which has a surface area of approximately 15 square meters per gram is obtained according to Example 1. The polypyrrole at 0.1 equivalents is placed in a glass reaction vessel which is sealed from the atmosphere. The polypyrrole has an equivalent weight of 509. Also added to the reaction vessel is 0.12 equivalent of potassium methoxide. Excess methanol provides additional solvent for the reaction. The potassium methoxide is extremely effective in removing protons from the polymer.

The reaction is maintained as close to 20° C. as is practical. The reaction is allowed to continue for a period of approximately 12 hours. Following this period of time, the deprotonated polypyrrole is filtered and washed in additional methanol.

Following the filtration and washing in methanol, the deprotonated polypyrrole is placed in an Soxhlet extractor for approximately 14 hours.

The deprotonated polypyrrole as obtained above has a surface area of approximately 50 square meters per gram.

EXAMPLE B

An aqueous mixture of 50.9 parts polypyrrole, and 1000 parts water from Example 1 is introduced to a sealed glass reaction vessel. The anion of the polymer is lauryl sulfate. The polypyrrole lauryl sulfate has an equivalent weight of 509. Potassium hydroxide (5.72 parts) is introduced to the aqueous mixture incrementally to provide an even reaction rate. The temperature of the reaction is maintained as close to room temperature as is possible.

The deprotonated polypyrrole is filtered, and washed in methanol, followed by stripping and drying of the filtrate. The deprotonated polypyrrole polymer is then dried in a vacuum oven.

EXAMPLE C

This example describes the reprotonation of a deprotonated polypyrrole.

Deprotonated polypyrrole (5 parts) is placed in a flask containing 50 parts of distilled water. With stirring at room temperature, 5 parts of concentrated hydrochloric acid are added over 30 minutes. The product is stirred at room temperature for 2 hours, then filtered and washed 3 times with distilled water. After drying in vacuum at 80° C. for 4 hours, 5.1 gms of a black, conducting polymer is obtained. Chloride analysis is 13.3% indicating incorporation of the proton as the hydrochloride salt of the polymer. The product has conductivity of 1 S cm$^{-1}$.

Substantially similar results are obtained in this Example by utilizing the polymers of Examples 2 through 20 which have been treated according to Examples A or B.

The preparation of the polyaniline is conveniently conducted as follows. The product will obtained as a dark blue/black powder corresponding to the hydrochloride salt of the formula:

The product is obtained by treating a one molar solution of aqueous hydrochloric acid containing dissolved aniline with an oxidizing agent such as ammonium peroxydisulfate. The protonation is completed by washing the powder with a one molar aqueous hydrochloric acid solution followed by drying under a dynamic vacuum (about 10 microns) at room temperature for several days to remove the water and HCl.

After this time, the conductivity of the polyaniline, as a compressed pellet, is determined. The conductivity is noted to decrease to a constant value of about 5 ohm$^{-1}$ per centimeter. An elemental analysis for the polyaniline shows that the product is about 97.5% by weight of carbon, hydrogen, nitrogen and chlorine and 0% sulfur. The analysis demonstrates that a maximum of one mole of hydrochloric moiety is combined with each monomeric repeating unit (containing two nitrogen atoms). The foregoing demonstrates the manner of obtaining the 2S form of polyaniline.

The protonated form can be converted to the substantially deprotonated form which is a dark purple/black powder exhibiting a metallic copper glint by stirring with a 0.5 molar solution of potassium hydroxide in a water/ methanol mixture followed by washing with a water/methanol mixture and drying under a dynamic vacuum as previously described. The conductivity of the copper-colored pellet is approximately 10$^{-11}$ per ohm per centimeter. The deprotonated polyaniline has the nominal formula:

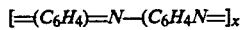

$$[=(C_6H_4)=N-(C_6H_4N=]_x$$

The elemental anaylsis of the deprotonated product shows that essentially all of the hydrogen chloride is removed by this procedure. The elemental analysis shows that the carbon, hydrogen, nitrogen and chlorine to be 97.37% of the product while sulfur is shown as a trace amount.

A further desirable variable in the present invention is to obtain the polymers as the protonated material followed by deprotonation of the polymer prior to their use in determining the acidic hydrogen concentration of the medium. It is often convenient to obtain the organic polymer in its substantially protonated form, followed by a substantially deprotonating the organic polymer, then followed by reprotonating the polymer to the desired degree. This process may be simply conducted as the polymers are typically obtained in their protonated form upon reaction of the monomer to form the polymer. Any convenient base, such as sodium hydroxide, potassium hydroxide or the respective alkoxides, particularly the methoxide, may be utilized to deprotonate the organic polymer. Thereafter, an acid such as dilute hydrochloric acid may be utilized to reprotonate the polymer to the desired degree. The processing scheme allows for the polymers to be freed of unwanted materials and also to obtain a greater degree of accuracy in the sensitivity of the acid sensor.

The polyaniline is most useful in an acid sensor for a lubricant when prepared as a partially protonated polymer. The partially protonated polymer is conveniently obtained by dispersing the substantially deprotonated polymer at a 1% by weight concentration in water which is adjusted to a pH of 2 to 4, preferably 2.5 to 3.5, more preferably 2.75 to 3.4, and most preferably form 2.9 to 3.1 at a temperature of 25° C. For a given partially protonated polymer the pH is maintained at the desired level by adding sufficient acid e.g. as the polymer takes up acid it depletes the available acid and the pH begins to rise. Typically the partial protonation will be conducted over a period of 6 hours (until equilibrium) followed by filtering off the solids, washing twice in acetone and vacuum drying.

The polypyrrole polymers are typically formed such that there is no need to protonate the polymer. However, the polypyrrole may be partially protonated as described herein, where desired.

The resistance of the partially protonated polyaniline polymer is typically $2.4 \times 10^6$ ohm per cm to $2.6 \times 10^6$ ohm per cm, at 55° C.; preferably $1.8 \times 10^6$ ohm per cm to $2.25 \times 10^6$ ohm per cm at 60° C.; more preferably $1.5 \times 10^6$ ohm per cm to $1.7 \times 10^6$ ohm per cm at 65° C. and also more preferably $1 \times 10^6$ to $1.05 \times 10^6$ ohm per cm at 70° C., when measured in an additive free oil of lubricating viscosity.

The polymers, as described herein, may be utilized in either their powder or solid form to prepare the sensor. It is desirable to obtain the organic polymer in a solid form to minimize inconsistencies due to utilizing a powder. To obtain the organic polymers as a solid, the materials may be placed in an appropriately sized die and subjected to a pressure between 400 kilograms (5680 psi) and 600 kilograms per square centimeter (8500 psi) of the largest surface of the polymer within the die. Conveniently, the pressure utilized to obtain the organic polymer in a solid form is from about 475 kilograms to about 525 kilograms per square centimeter (6740–7450 psi) of the largest surface area in the die. It is possible to use physical mixtures of polymers with multiple leads to the ohm meter, however, such is not necessary. Physical mixtures of polymers with multiple leads may be used to measure different sensitivities of the acidic hydrogen concentration of the medium for different conditions such as greater temperature sensitivity when an engine is running hot as opposed to its start up temperature.

It is desirable when determining the acidic hydrogen concentration by means of an ohm meter that the current utilized to determine the resistance of the organic polymer be applied on a noncontinuous basis. While the present invention allows for the measurement of acidic hydrogen concentration on a continuous, in situ basis in the medium, it has been observed that the organic polymers have a longer useful life with greater precision in the measurements of acidic hydrogen concentration if the polymer is not continuously subjected to the electric current to measure resistance. Thus, a timing mechanism may be utilized so that the acidic hydrogen concentration is measured by impressing a current on the polymer at varying time intervals. It is suggested that as the acidic hydrogen concentration is more likely to be accurately measured when the engine is warm, that during the first five minutes of operation the acid number not be measured and that successive five or ten minute intervals be utilized to determine the acidic hydrogen concentration.

The manner of notifying the operator that the base reserve has been substantially depleted may be by means of a direct readout on an ohm meter appropriately calibrated, or by means of a warning light simply advising the operator that the oil is no longer in a serviceable condition.

It is further a desirable situation that the organic polymer be substantially free of metal or graphite or other conducting particles. This is because the present invention operates on the assumption that the only factor affecting the resistance of the organic polymer is the acidic hydrogen concentration as taken up by the polymer. Thus, metallic, graphite or other conducting particles, which may be (e.g. copper) leached into the medium from the organic polymer, or conversely, from the medium to the polymer surface or interior are deleterious to the accuracy and precision with which the acidic hydrogen concentration may be measured.

It is also desirable that when the organic polymer is located within the medium that the greatest exposed surface area of the organic polymer should be substantially coincidental to the gravitational vector. Stated otherwise, the organic polymer will typically have at least two leads (e.g., to and from the ohm meter) and these leads will be spaced apart from one another lengthwise on the organic polymer. Where a lubricating oil is used in an engine, it will frequently be observed that various organic and inorganic materials may either block the surface of the polymer from absorbing and absorbing the acidic hydrogen or may penetrate the polymer and become a conductant which eventually will have the effect of shorting out the organic polymer.

The method of avoiding these adverse effects is to locate the polymer such that the gravitational forces have a minimal effect of depositing materials from the lubricating oil onto the polymer surface. It is, of course, envisaged that the organic polymer may be shielded from contaminants so long as the acidic hydrogen within the medium are available for contact with the organic polymer.

In one embodiment of the invention, the organic polymer may be placed within a portion of a vehicle oil filter where it is shielded from gross contaminants. A further variation on this method is to mount the organic polymer within the filter such that the organic polymer assumes a position substantially coincidental to the gravitational vector. Self-positioning of the organic polymer may be accomplished, for example, in a motor vehicle by movably mounting the organic polymer. One method of movably mounting the organic polymer is through the use of flexible leads to the ohm meter such that when the engine is not in operation, the gravitational effect will orient the organic polymer toward the gravitational vector. The same effect may be beneficial as many oil filters have a different direction of flow than the gravitational vector. In such a case, the flexible leads to the organic polymer would allow for the polymer to orient itself in the fluid stream of the medium on which the acidic hydrogen concentration is to be measured and when the engine is at rest to orient the organic polymer substantially coincidental to the gravitational vector. The organic polymer may be used as a powder or film or compressed solid. Preferably, the organic polymer within the acid sensor is in a solid, non-pulverant state such as the compressed solid.

In line with the foregoing, it is desirable that the maximum dimension of one of the two minor axis of the organic polymer be less than 0.65 mm at its greatest point. The greatest axis of the organic polymer is conveniently up to about 25 mm at its greatest point, preferably up to about 20 mm, and most preferably not greater than 17 mm. It is further noted that the two minor axis of the organic polymer may be, and are preferably substantially the same. The organic polymer may also be in the form of a cylindrical pellet. As the pellet is conveniently 0.75 cm to 1.8 cm, preferably 0.9 cm to 1.6 cm in diameter. The polymer is conveniently as thin as possible with a suggested thickness of the disc of about 0.1 mm to 2 mm, preferably about 0.4 mm to about 1.5 mm.

A further embodiment of the location of the organic polymer utilized to measure the acidic hydrogen concentration is within the oil drain plug of a vehicle engine. The oil drain plug is ordinarily located at the lowest point within the engine to facilitate drainage of the oil on a substantially complete basis. The drain plug is a desirable location as it may be easily changed whenever the lubricating oil is changed. Where a drain plug is utilized as the site of the organic polymer, it is desirable that the organic polymer be located such that it is above the center point of the drain plug when the latter is installed in the crankcase. This location of the organic polymer in the drain plug is desirable to avoid contaminants from contacting the organic polymer as previously described. It can easily be seen that if the organic polymer were located on the lower side of the drain plug that contaminants would be maximized in their ability to contact the organic polymer. The location of the organic polymer either permanently or detachably mounted to the drain plug allows for easy replacement or cleaning of the organic polymer.

The leads (wires) to the organic polymer are conveniently shielded to avoid shorting out. The contact point of the leads within the organic polymer are exposed to allow transfer of current to adequately determine resistance. The organic polymer in a drain plug is desirably physically protected to avoid damage during installation. The location within an oil filter is conveniently such that the organic polymer is continuously in the oil.

The acid sensor may be permanently located in the engine although this makes replacement difficult. The use of the acid sensor in a gas stream may be at any convenient point. When the acid sensor is removable standard male-female electrical couplings may be employed. The terminals on the acid sensor are conveniently at the furthest points on the organic polymer and a line there through is substantially coincidental to the gravitational vector.

EXAMPLE AA

A deprotonated sample of polyaniline is dispersed at 1% by weight in water previously adjusted to pH 3 with dilute hydrochloric acid. The water is continuously stirred and the pH maintained at 3 by periodic additions of the acid. The polymer is reprotonated to the described degree when the pH fails to rise following adjustment. The polymer is then dried. The mixture of the polymer is determined after preparing at 1.2 cm diameter disc the polymer which is 0.38 mm (0.015 inch) thick. The disc is obtained by placing 0.0625 grams of the desired product in a die and applying 493 kg/cm$^2$ (7,000 psi) pressure.

The disc is then used in an oil filter or drain plug substantially as shown in the drawings. The disc is calibrated to show the point at which the oil becomes acidic.

Substantially similar results are obtained when the polymer of Example B is employed.

The gravitational vector shows that this particular oil filter has been mounted at approximately a 45° angle to the engine and that the acid sensor 1 has aligned itself when the engine is not running such that it is substantially coincidental to the gravitational vector. Lead 5 has sufficient slack to allow the acid sensor 1 to pivot about the point of attachment 2 when the engine is in operation. Thus, when the engine is not engaged in operation, the acid sensor 1 is not subjected to undue contamination by large particles of sediment present in the filter.

Figure 1:
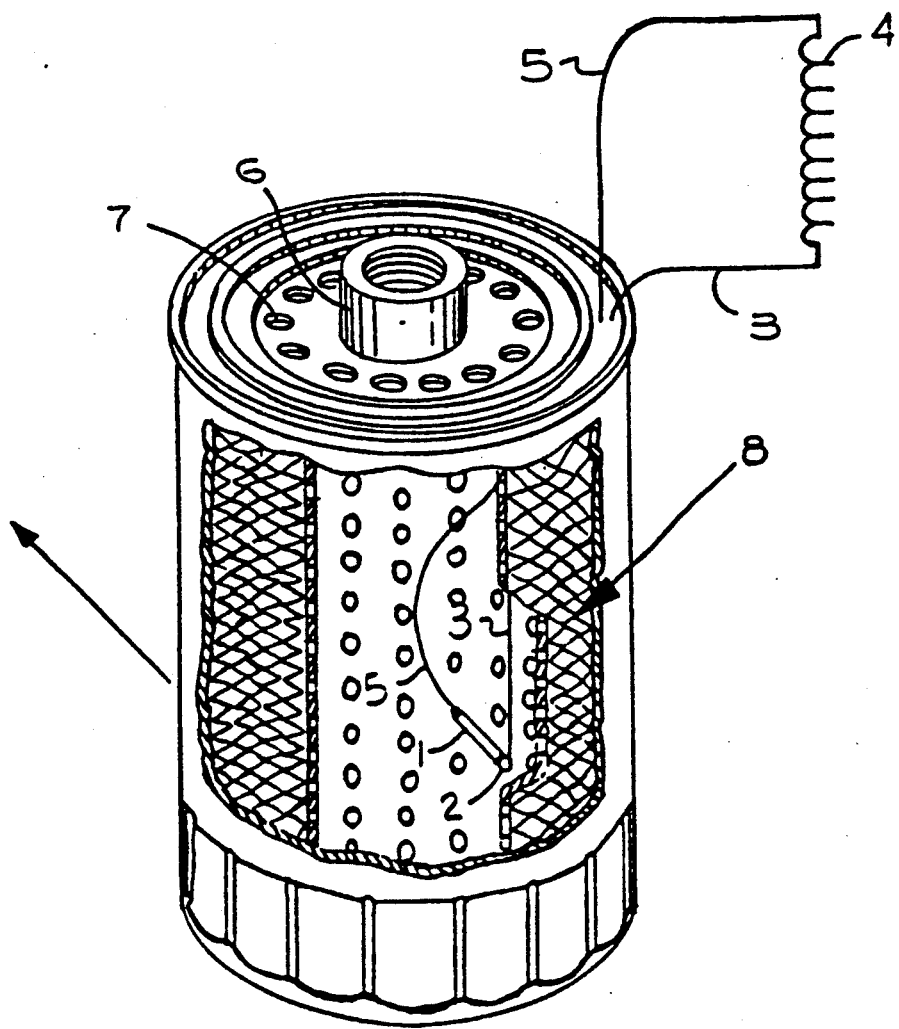
FIG. 1 is an exploded view of a conventional oil filter. The acid sensor (organic polymer) is shown as 1. The acid sensor 1 is movably mounted at 2 to the interior of the oil filter. Lead wire 3 is attached to one side of the ohm meter 4 to sense differences in conductivity (resistance) of the organic polymer related to increase in acidity of the lubricating oil. Lead 5 is the remaining lead from the ohm meter to the acid sensor. The flow nozzle 6 to the internal combustion engine (not shown) returns the oil for use in the engine. A plurality of spaced orifices, 7 are used to deliver the oil to the oil filter wherein the oil is passed through the filter material 8, and past the acid sensor 1 before being returned through orifice 6 to the engine.
Figure 2:
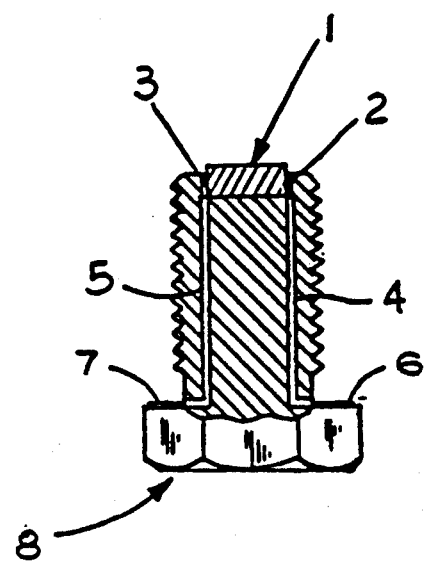

FIG. 2 shows an embodiment of the present invention utilized as a replaceable drain plug for a motor vehicle. The acid sensor 1 is shown as mounted on the drain plug 8 such that the overall dimensions of the acid sensor are less than the diameter of the threaded portion of the drain plug. Orientation of the acid sensor 1 in this manner avoids damage to the acid sensor during installation. Points 2 and 3 show the attachment of the acid sensor to leads 4 and 5 to an ohm meter (not shown) wherein the leads are embedded in the drain plug. Six (6) and 7 show conducting means for leads 4 and 5, respectively to be taken off to the ohm meter for determination of the resistance (conductivity). Also not shown are the paired leads on the bottom of the crankcase whereby 6 and 7 make contact with the leads to the ohm meter. In practice, points of contact 6 and 7 will be oriented on the engine block such that when the drain plug is threaded into the crankcase that proper contact is made. Leads 4 and 5 are typically shielded to avoid conductivity through the drain plug 8 which is typically a ferrous material.

What is claimed is:

1. A polymer article comprising a partially protonated polyaniline polymer having a thickness in the range from about 0.1 to 2 mm, wherein the greatest axis of the article is up to about 25 mm.

2. The article of claim 1 in the form of a cylindrical pellet.

3. The article of claim 1 in the form of a disk.

4. The article of claim 3 wherein the disk has a thickness in the range of about 0.4 to about 1.5 mm.

5. The article of claim 1 wherein the polymer has a resistance to the flow of electrons in the range of from about $2.4 \times 10^6$ to $2.6 \times 10^6$ ohm/cm measured at 55° C. in an additive-free oil of lubricating viscosity.

6. A polymer article comprising a solid partially protonated polyaniline polymer in the form of a cylindrical disk having a diameter in the range from 7.5 to 18 mm and a thickness in the range from about 0.1 to 2 mm.

7. The article of claim 6 wherein the article has a thickness in the range from about 0.4 to about 1.5 mm.

8. The article of claim 6 wherein the polymer has resistance to the flow of electrons in the range from about $2.4 \times 10^6$ to $2.6 \times 10^6$ ohm/cm measured at 55° C. in an additive-free oil of lubricating viscosity.

9. The article of claim 6 wherein the article has a resistance to the flow of electrons in the range from about $1.5 \times 10^6$ to $1.7 \times 10^6$ ohm/cm measured at 65° C. in an additive-free oil of lubricating viscosity.

10. A solid partially protonated polyaniline polymer product prepared by:
    (A) deprotonating a polyaniline polymer by treating the polymer with a base and
    (B) reprotonating the deprotonated polymer obtained as a product of step (A) by treating the deprotonated polymer with an acid.

11. The polymer product of claim 10 wherein the base of (A) is sodium hydroxide, potassium hydroxide, sodium alkoxide, or potassium alkoxide, or a mixture thereof and the acid of (B) is hydrochloric acid.

12. The polymer product of claim 10 wherein step (B) comprises:
    (1) dispersing 1% by weight of the polymer obtained from step (A) in water adjusted to a pH of from 2 to 4 measured at a temperature of 25° C. and
    (2) maintaining the polymer-containing water of step (1) at a pH in the range from 2 to 4 measured at a temperature of 25° C. by adding acid to the polymer-containing water.

13. The polymer product of claim 10 wherein the polymer product has resistance to the flow of electrons in the range from about $2.4 \times 10^6$ to $2.6 \times 10^6$ ohm/cm measured at 55° C. in an additive-free oil of lubricating viscosity.

* * * * *